United States Patent
Nicolet et al.

(10) Patent No.: US 11,484,249 B2
(45) Date of Patent: Nov. 1, 2022

(54) METHOD AND TOOL FOR MEASURING OSSEOUS QUALITY

(71) Applicant: BIEN-AIR HOLDING SA, Biel/Bienne (CH)

(72) Inventors: Daniel Nicolet, Biel/Bienne (CH); Yann Gâteau, Biel/Bienne (CH); Davide Sarchi, Zürich (CH)

(73) Assignee: BIEN-AIR HOLDING SA C/O BIEN-AIR DENTAL SA, Bienne (CH)

( * ) Notice: Subject to any disclaimer, the term of this patent is extended or adjusted under 35 U.S.C. 154(b) by 0 days.

(21) Appl. No.: 17/423,968

(22) PCT Filed: Feb. 3, 2020

(86) PCT No.: PCT/EP2020/052644
§ 371 (c)(1),
(2) Date: Jul. 19, 2021

(87) PCT Pub. No.: WO2020/157340
PCT Pub. Date: Aug. 6, 2020

(65) Prior Publication Data
US 2022/0039738 A1 Feb. 10, 2022

(30) Foreign Application Priority Data
Feb. 1, 2019 (EP) .................................... 19155145

(51) Int. Cl.
| A61B 17/16 | (2006.01) |
| A61B 5/00 | (2006.01) |
| A61C 1/00 | (2006.01) |
| A61C 1/12 | (2006.01) |
| A61B 90/00 | (2016.01) |

(52) U.S. Cl.
CPC .......... *A61B 5/4509* (2013.01); *A61B 5/0004* (2013.01); *A61B 5/4542* (2013.01); *A61B 5/7278* (2013.01); *A61C 1/003* (2013.01); *A61C 1/0007* (2013.01); *A61C 1/12* (2013.01); *A61B 5/682* (2013.01); *A61B 2090/066* (2016.02)

(58) Field of Classification Search
CPC ........ A61B 2090/062; A61B 2090/064; A61B 2090/066; A61B 17/1624; A61B 17/1615; A61B 17/1695
See application file for complete search history.

(56) References Cited

U.S. PATENT DOCUMENTS

| 6,763,257 B1 | 7/2004 | Rosholm et al. |
| 7,878,987 B2 | 2/2011 | Hansma et al. |
| 2003/0057947 A1 | 3/2003 | Ni et al. |
| 2008/0300510 A1 | 12/2008 | Schwyn et al. |
| 2011/0245833 A1* | 10/2011 | Anderson ........... B25B 23/0064 606/80 |
| 2018/0153466 A1 | 6/2018 | Ploy et al. |

FOREIGN PATENT DOCUMENTS

| JP | 2000245736 A | 9/2000 |
| WO | 2008052367 A1 | 5/2008 |
| WO | 2012083468 A1 | 6/2012 |

OTHER PUBLICATIONS

International Search Report and Written Opinion in PCT/EP2020/052644 dated Apr. 23, 2020, 12 pages.

* cited by examiner

*Primary Examiner* — Michael J D'Abreu
(74) *Attorney, Agent, or Firm* — Pearne & Gordon LLP

(57) ABSTRACT

The present invention relates to a device and a method for measuring osseous quality.

12 Claims, 11 Drawing Sheets

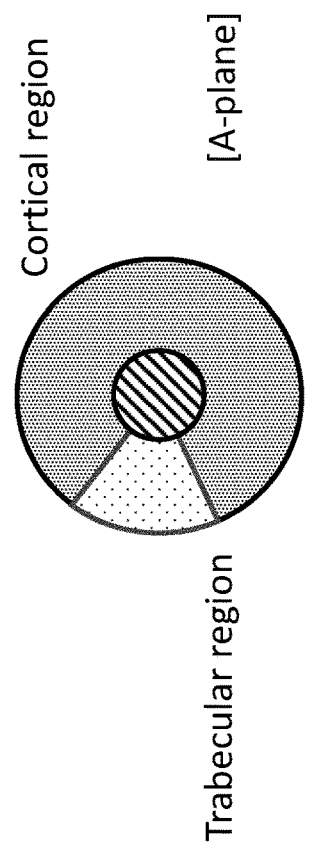
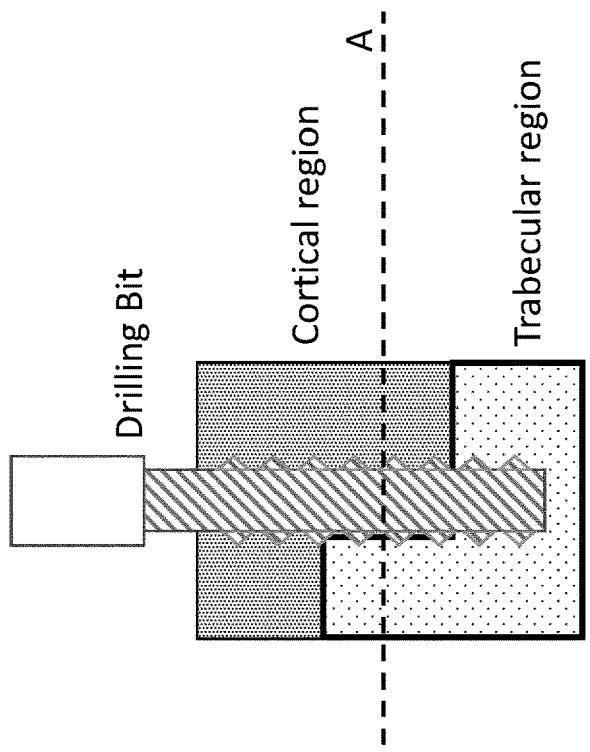
Fig. 8b
Fig. 8a

METHOD AND TOOL FOR MEASURING OSSEOUS QUALITY

TECHNICAL FIELD OF THE INVENTION

The present invention relates to the field of surgery, more specifically dental surgery and implantology.

STATE OF THE ART

In the context of methods for determining osseous quality, it is possible to classify two types of evaluation methods: The invasive methods, on the one hand, that is to say those which are based on empirical data obtained during a drilling of the bone whose quality is to be evaluated, and, on the other hand, the non-invasive methods using, for example, medical imaging techniques such as X-raying or magnetic resonance imaging (MRI).

A method of evaluation of the osseous quality (that is to say the mechanical resistance) to be carried out during preparation of the site for the placement of an implant is described in the patent document WO2008052367. This document specifies that a hole is made in the bone and that a specific instrument is then used to determine properties of mechanical resistance of the bone. The properties to be characterized are, on the one hand, the mechanical deformation induced by a pressure exerted on the interior of the hole, and, on the other hand, the twisting moment or torque to be applied to a tool inserted in the hole to deform the hole mechanically.

A similar method adapted this time to the case of bones of large dimensions, such as the femoral bone, is disclosed in the document WO2012083468, which also discloses a handpiece adapted to this procedure: in this case the mechanical resistance of the bone is measured by making the drilling tool turn in the direction opposite to the direction of drilling to correlate the mechanical deformation of the hole and the torque applied. The drilling tool has moreover a symmetrical form, which means that it can extract the material in two directions of rotation: the first direction for the cutting, and the second direction for the measuring. For this reason, this method is not suitable for the case of a dental implant because the rotation in the opposite direction for the measurement risks fracturing or damaging the bone. In fact, all the drill bits and drills for the preparation of dental implants have a screwing direction and an unscrewing direction, the unscrewing direction allowing the removal of the drilling tool without causing tearing away of osseous material.

The document U.S. Pat. No. 7,878,987 proposes, for its part, a specific alternative solution for mini-invasive evaluation of the resistance of the whole bone to fractures. In this case the system is able to pass through the skin and the soft tissue of the patient before reaching the surface of the bone. Then the measurement is carried out by pushing a very fine test blade/probe inside the bone (indentation, without rotation of the probe). The measurement of the force applied to the blade/probe to penetrate the bone and to be extracted makes it possible to establish an evaluation of the risk of fracture of the bone.

However, there does not exist any method specifically adapted to dental implantology for evaluation of the quality of a bone.

Currently, in this specific technical field, the only recognized methods for a qualitative evaluation of the osseous quality of bone for dental implant are the non-invasive methods such as those described below:

The patent document JP2000245736, which describes a tool for detecting osteoporosis using microwaves.

The American patent document U.S. Pat. No. 6,763,257 of ROSHOLM ET AL. describes a method of osseous quality evaluation using radiogrammetry;

The American patent application US2003/0057947 of NI ET AL describes a technology based on magnetic resonance for determining the porosity of a bone.

These non-invasive methods do not provide however any quantitative measurement of the osseous quality and are therefore considered as being too imprecise to be used to define an optimal implant strategy, because they do not make it possible to define a sufficiently precise spatial profile of osseous quality.

Thus there exists a need for solutions not having these known limitations.

SUMMARY OF INVENTION

An object of the present invention is to propose a new measuring device as well as a new method for determining osseous quality which is more precise and more effective.

More specifically, an object of the present invention is to provide a clear spatial profile of the different osseous regions without necessitating additional measurement steps with respect to usual operating procedures nor requiring specific instruments nor specific manipulations.

The objects are attained by means of the features of the main device claim 1.

An advantage of the proposed solution is that it introduces a method making it possible to measure quantitatively the osseous quality during the drilling for preparation of the site of the dental implant. This procedure makes it possible to use a standard implantology kit, made up of a micro motor and a contra-angle reducer (generally with a gear ratio of 20:1) without having to add specific devices.

Such a method furthermore makes it possible to carry out a series of measurements during all the phases of preparation of the implant, without having to add supplementary operational phases nor to expose the patient to operations more invasive that the traditional drilling operations. In particular, no deformation through pressure and/or torsion (as required in the context of the solution disclosed in the WO2008052367) is necessary.

Another important advantage provided by the proposed solution concerns the precision of the proposed quantitative measurement. In other words, the latter makes it possible not only to classify the osseous quality at the implant site but also to reconstruct the spatial profile of the osseous quality from the surface of the bone to its depth. More specifically, the measurements obtained provide a precise spatial profile of the osseous quality, from the surface of the bone towards the interior of the bone, and identify the zones of transition from the cortical region, that is to say the hardest region, near the outer surface of the bone, to the softer trabecular or apical region at the inside of the bone.

According to a preferred embodiment for the present invention, the bone quality is derived directly from current derivative measurements, without ever measuring the current directly. This allows for a simplification of the calculation process, dispensing with the need to post-process the current signal in order to obtain a torque value, and in turn a derivative of the torque yielding the bone quality.

According to another preferred embodiment for the present invention, the drilling tool has a variable diameter profile ranging between a minimal and a maximal value, the ratio between the minimal and the maximal value being at least equal to 2. In this case, the derivative of the current and of the torque can be assumed to be only dependent on the portion of the drilling tool having the maximum value of the diameter. The quantity $L_F$ (or $L_f$) defines the length of the portion having the maximum diameter. The ratio between the maximum and the minimum diameter must be equal or larger than 2 in order to guarantee that the spatial behavior of the current derivative only depends on the penetration depth of the maximum diameter portion of the drilling tool.

According to yet another embodiment for the present invention, the device for measuring bone quality further comprises an angular sensor such as a Hall sensor, a magnetic sensor, an optical or an electrical sensor in order to know the exact orientation of the rotor of the contra-angle, and an indexation system in order to determine the exact orientation of the drill bit. Thus, while ensuring that enough measurement data are gathered each time the drilling bit has made a complete revolution—e.g. an order of magnitude of 10—it is possible to additionally obtain an angular distribution of the bone quality.

According to yet a further embodiment for the present invention, the device for measuring bone quality comprises a non-circular asymmetrical drill bit, yielding an extruded diameter is at least 20% greater than the mean diameter of the drill bit. Thanks to such a special drilling tool, it is possible to obtain a 3D representation of the bone quality, because it is possible to know not only the variation of the bone quality as a function of the penetration depth, but also as a function of the angular orientation.

According to a variant embodiment for the present invention, the device for measuring bone quality may further encompass a calibration and benchmarking tool, allowing to define classification criteria according to a specific drilling bit, handpiece or motor.

BRIEF DESCRIPTION OF DRAWINGS

The present invention will be better understood from reading the description which follows, given by way of example, and with reference to the drawing in which:

FIGS. 7A and 7B show the same figures as 6A and 6B when the drilling operation is performed with a special drill whose length of maximal diameter $L_f$ is equal to 0.5 mm, such as a drill illustrated on previous FIG. 4a;

FIGS. 8A and 8B show two section views of the transition region between a cortical and a trabecular region of a bone; respectively a sagittal section view, and a horizontal section along the horizontal plane A-A illustrated on FIG. 8A.

DETAILED DESCRIPTION OF THE INVENTION

In the context of this application, the expression "contra-angle" is used as a generic term designating any working tool of a practitioner, in particular a dental surgeon. Likewise, the term "motor" designates in a universal way a device able to create a mechanical movement (in particular a rotational movement, but possibly also a linear, oscillating, etc. movement), transmitted to the drilling tool by means of the kinematic chain integrated in the contra-angle whose gearing determines a predefined reduction coefficient. The expression "drill bit" or "thread tap" is used as a generic term designating any tool for drilling bone, irrespectively of its model and its dimensional features.

Described in the following will be a preferred embodiment connected to the field of dental implantology. Such an electronic device for controlling motors for implantology is made up of a connection box to the motor and of a peripheral interface for the user (the two being able to be removable or non-removable, with respect to one another, by the user), characterized by the following features:

1. A function, able to be selected by the user, activates the recording instantly, i.e. in real time, of the electric current consumed by the motor.

2. In the memory of the box or of the peripheral, post-processing algorithms, described in the following, link the signal in real time of the electric current consumed by the motor to the signal of the torque applied to the drilling tool as a function of position, in depth, of this tool.

3. A tool for transferring data to another electronic device, this transfer tool being a WIFI emitter or a connection gate via cable.

Figure 1:
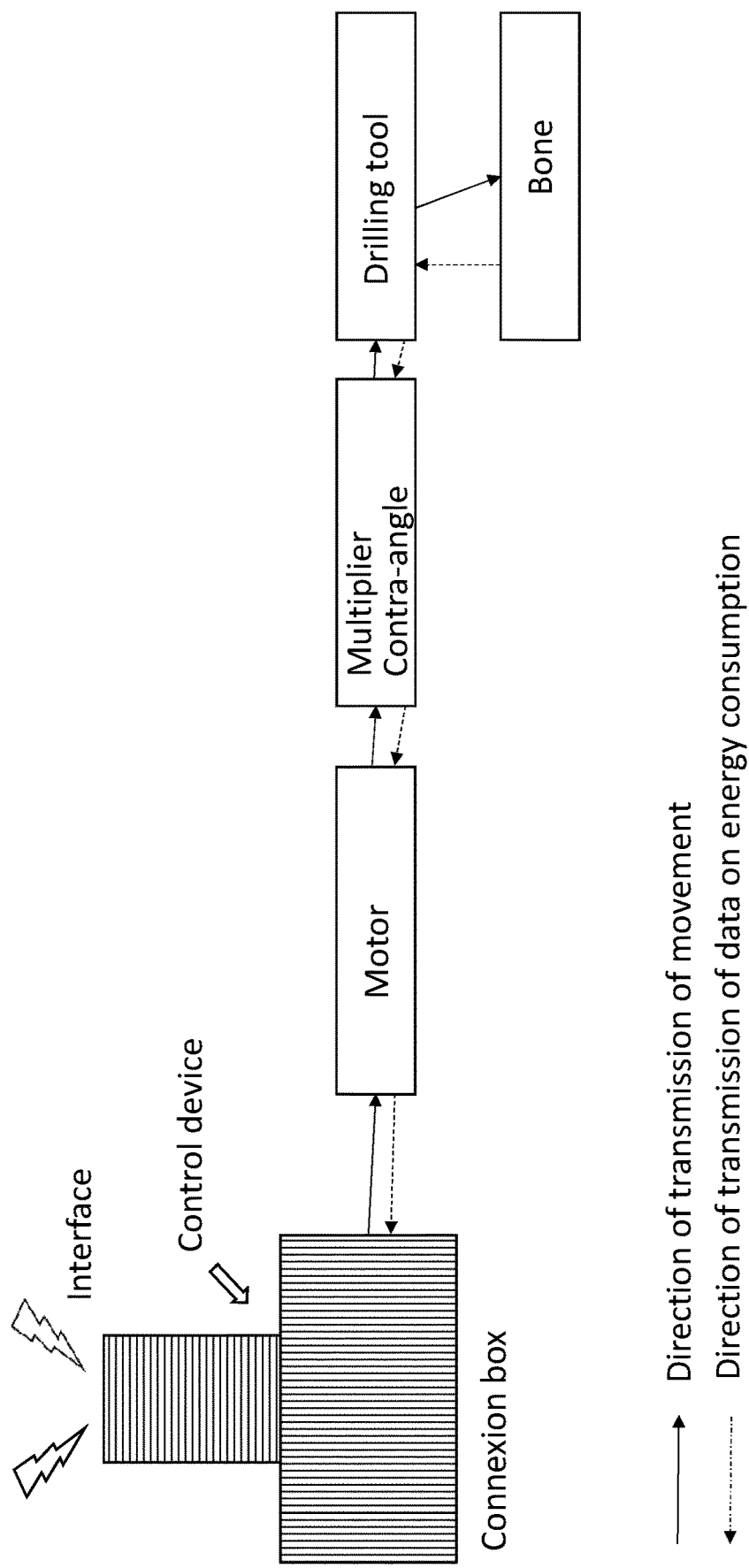
FIG. 1 is a logical schema of the different functional parts of a measuring device according to a preferred embodiment of the present invention.

The device and the measuring method are illustrated in FIG. 1 in a schematic diagram showing the device with the transmission chain from the motor to a drilling tool applied to the bone and the return of measurement data. The arrows with unbroken lines indicate the direction of transmission of movement, while the arrows with dashes, in opposite direction, show the direction of transmission of the information concerning the consumption of energy. In this figure, the transmission via the communication interface is carried out wirelessly (the lightning bolts indicating communication with any suitable technology, such as Wi-Fi, UWB, etc.), and, according to this preferred embodiment, the functional unit for measuring instantly the current consumed by the motor is structurally integrated into the box of the control device; according to a variant, this unit could even be miniaturized and integrated into the motor.

During the procedure for measuring the osseous quality of the dental implant site, the user of the implantology kit can first of all select, via the control console of the motor, the option whereby, during at least one of the drillings of the bone necessary for the preparation of the implant site, the electric current consumed by the motor is recorded in the memory of the motor connection box or of the peripheral used as interface (for example, a digital tablet). The control console (not illustrated) preferably comprises a display unit in the form of an LCD screen and keys or a wheel to select menus and/or programs and to validate the choices made by the surgeon.

Then the signal in real time of the electric current consumed by the motor is post-processed by algorithms preferably installed on the motor connection box or the peripheral used as interface. In such a preferred embodiment, the unit for processing data collected during the drilling operation is thus integrated in the box; however, depending upon the needs and as a function of constraints in terms of processing capacities, a processor situated in a remote computer could also be used. In this case, the interface for data transmission must nevertheless offer a speed sufficiently great so as not to constitute a limiting factor. The signal processing can use, for example, local regression, Savitzky-Golay, moving average, Gaussian filtering, etc. According to an advantageous embodiment, the signal processing can also eliminate the constant contribution connected to the no load consumption of the motor as well as the pressure exerted by the user, which in reality constitutes only an "offset", that is to say a shift of the immediate consumption curve by a constant.

Each of the motors has a rated power, in watts, which constitutes the maximal possible power that this motor can generate. During the drilling phases, in general, the power used, able to be determined directly from the current values since the voltage itself remains constant, does not exceed 10 to 15% of this rated power. On the contrary, during the phases of screwing of the implant, much higher values up to 80%, even more, of this rated power can be achieved.

The post-processed signal of the electric current, which establishes, first of all, the connection between the immediate power of the motor and the immediate torque (which is exerted on the bone by the drill bit via the kinematic chain of transmission), makes it possible in a second phase, by using the type of drill bit and the speed of drilling, to then represent the torque applied to the drilling tool as a function of position, in depth, of this tool, this signal being either recorded in the memory of the motor connection box or of the peripheral, or transmitted by cable or WIFI to another electronic device.

In other words, the speed of the motor, which is generally applied via a specific program and controlled by a console—typically between 100 and 1000 revolutions per minute (rpm)—has only very slight deviations of less than 1% during the drilling operations, on the one hand, and, on the other hand, this motor speed, combined with the gear ratio of the contra-angle used (generally 20:1) and the type of drill bit used as drilling tool—in particular its screw thread—make it possible to correlate unequivocally the drilling time to an associated depth.

Figure 3B:
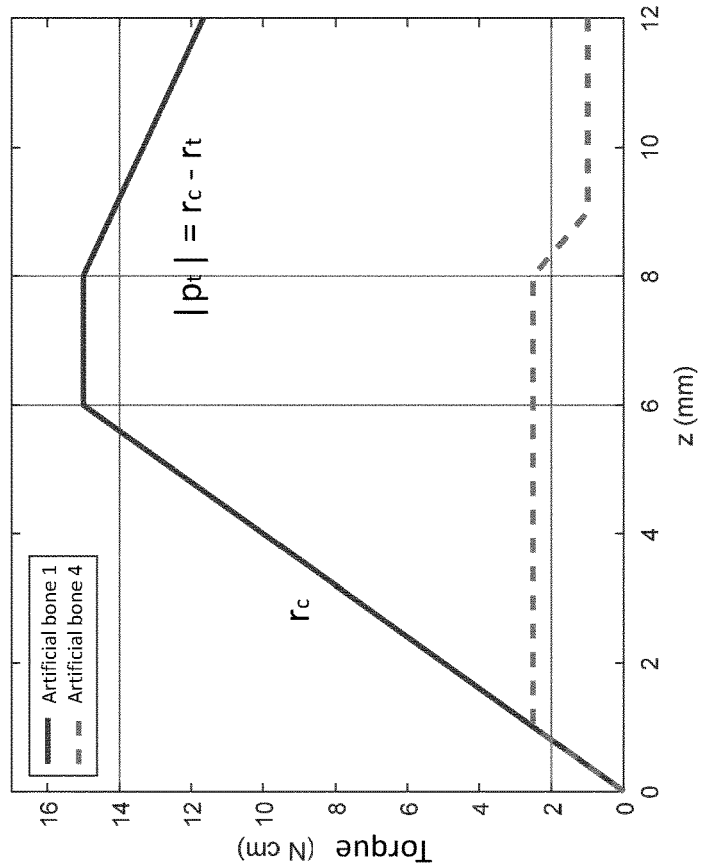
FIGS. 3A and 3B show respectively graphs of current consumption by a motor according to the present invention for two different types of artificial bone as a function of time, and a schema of the torque exerted by the motor as a function of the depth in each of the two bones according to an embodiment of the present invention.
Figure 3A:
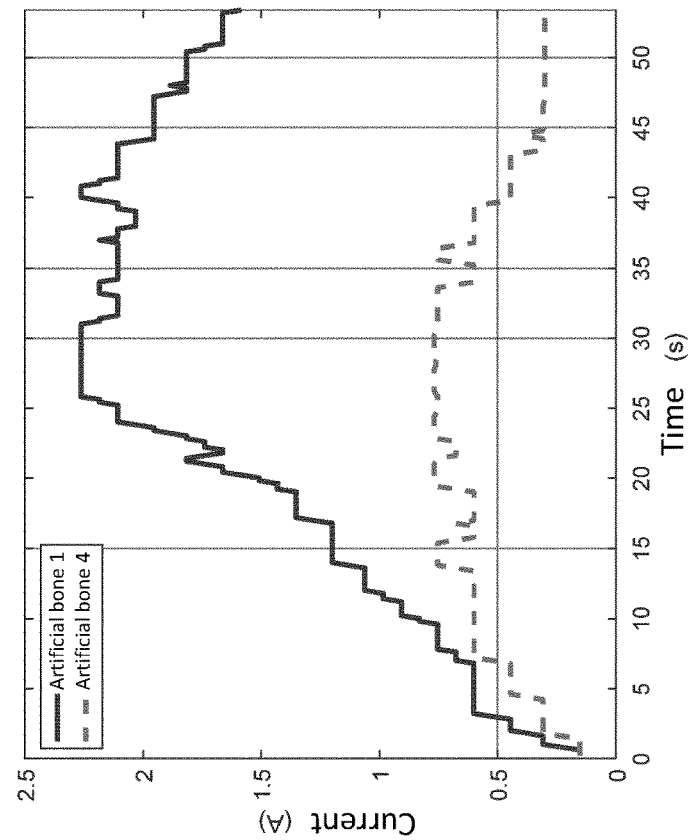

Therefore, as will be seen in light of the correspondence of FIGS. 3a and 3b, the proposed method of determination of osseous quality thus makes it possible to transform the input data, consisting of:

i. the post-processed signal of the electric current;
ii. the drilling tool model used;
iii. the operational speed of the motor;

into notably the following output data:

a. the signal of the osseous quality as a function of the depth inside the bone;
b. the depth of the transition between cortical region and trabecular region of the bone;
c. the average osseous quality in the cortical region;
d. the average osseous quality in the trabecular region;
e. the confidence coefficient, number between 0 (low confidence) and 1 (high confidence), relating to the value of the average osseous quality in the cortical region. In a preferred embodiment, this coefficient is a function of the correlation coefficient between torque and depth in the cortical region, of the remainders of the polynomial regression in the cortical region and of the signal to noise ratio in the cortical region.
f. the confidence coefficient, number between 0 (low confidence) and 1 (high confidence), relating to the value of the average osseous quality in the trabecular region. In a preferred embodiment, this coefficient is a function of the correlation coefficient between torque and depth in the cortical region and in the trabecular region, of the remainders of the polynomial regression in the cortical region and in the trabecular region and of the signal to noise ratio in the cortical region and in the trabecular region. The confidence in the trabecular region is generally less because the calculation depends on the quality of the signal in the two regions, cortical and trabecular. The method described makes it possible however to quantify mathematically the degree of confidence in this region.

Figure 2B:
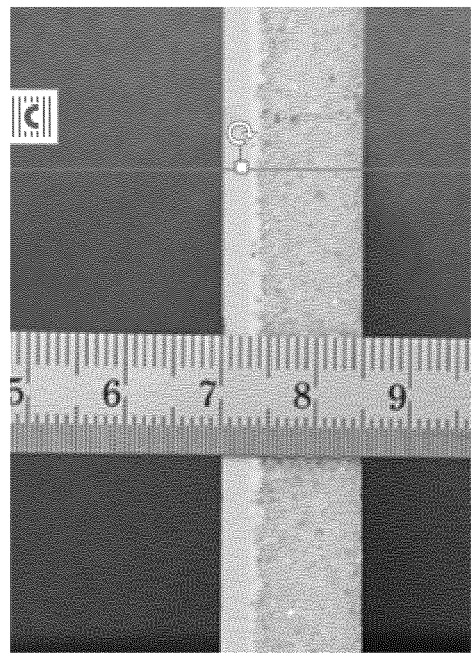
FIGS. 2A and 2B show schematically a drill bit as conventionally used in the field of dental implantology and a sectional view of an artificial bone highlighting the cortical and trabecular zones.
Figure 2A:
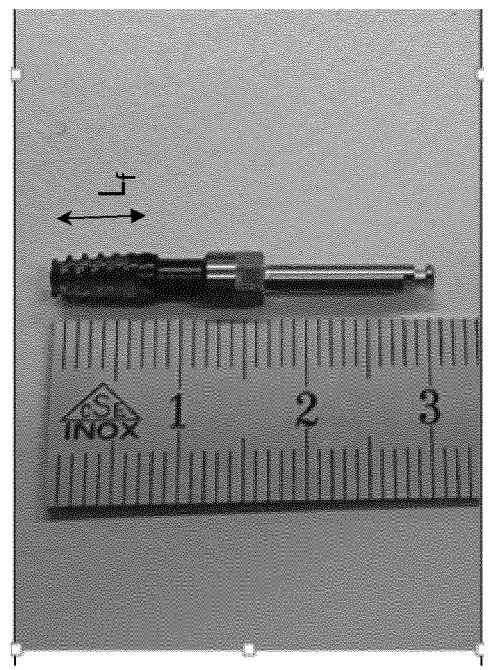

FIG. 2a shows a typical drilling tool (a thread tap), whose drilling length is approximately 8 mm, and comes to a stop at 12 mm, while FIG. 2b shows a commercially available artificial bone (similar to the composition of a real bone): it has a denser and harder region of 4 mm, combined with a softer region of 11 mm.

Shown in FIGS. 3a and 3b is an example of post-processed measurements according to the method described above.

The signal of the current consumed as a function of time, illustrated by FIG. 3a, was post-processed and linked to the signal of torque as a function of depth in the bone at the tip of the drilling tool, inferred from FIG. 3b as a function of the above-mentioned input parameters (motor speed and type of thread tap used as drilling tool). The separate measurements illustrated in the two superimposed graphs in each of these FIGS. 3a and 3b have been made for two types of artificial bone:

Type 1: thickness of the cortical region equal to 6 mm and trabecular region of good quality,
Type 4: thickness of the cortical region equal to 1 mm and trabecular region of poor quality.

The parameters describing the output data are directly visible on the graph:

The artificial bone 1 and the artificial bone 4 have a cortical osseous quality corresponding to a drilling resistance rc=25 N (same initial slope of the curve).

The artificial bone 1 has a cortical thickness of 6 mm (position of the start of the plateau), whereas the artificial bone 4 has a cortical thickness of 1 mm (start of the plateau).

The negative slope pt=dC/dz which follows the plateau ending at 8 mm, in other words the total length of the thread tap used, makes it possible to determine the osseous quality of the trabecular region by means of the relationship: rt=rc−|pt|.

It can thus be deduced from these measurements that the artificial bone 1 has a high trabecular osseous quality, corresponding to a drilling resistance rt=16.5 N (pt=−8.5 N), whereas the artificial bone 4 has a lower trabecular osseous quality, corresponding to a drilling resistance rt=10 N (pt=−15 N).

For each of the detection steps of the 3 phases above, i.e. a first linear rise, then a plateau, and finally a still linear decline, a polynomial curve fitting could preferably be achieved.

According to a preferred embodiment for the present invention, the electronic device for controlling implantology motors contains moreover, installed in the memory of the box or of the peripheral, an algorithm linking the post-processed signal of the electric current and the model of drilling tool used to a discrete parameter (whole numbers) for classifying osseous quality, corresponding, for example, to classifications of BMI (Bone Mass Index) or BMD (Body Mineral Density) type, which are expressed by a continuous variable but used in practice by assessing these values with respect to categories/ratings based on experience and the statistical results separating different 'classes'.

It is thus possible to connect with the measurement obtained by the proposed method a discrete variable rating (1, 2, 3, 4, . . . ) of the osseous quality, permitting an easy typological ranking of the results obtained as a function of the risk associated with the implant placement (for example: quality 1 corresponding to a resistant implant/very slight risk; quality 2: stable implant, low risk; quality 3: potentially unstable implant, high risk; quality 4: unstable implant, very high risk).

According to a preferred variant for the electronic device for controlling implantology motors, as illustrated in the rest of FIG. 1, an interface is available for the transfer of data to another electronic device, the transfer tool being preferably made up of a WIFI emitter in order to avoid any unnecessary additional cable.

Still according to a preferred implementation variant for the device and the method according to the invention, it is possible for the surgeon to select the input data constituted by "the model of drilling tool used" directly via the interface peripheral, that is to say the console, from among a plurality of possible models depending upon personal preferences or operational constraints. The measurement can in fact be carried out by using special drilling tools, characterized by a section of variable diameter, by at least a factor of 2, along the axis of the tool, the maximum diameter being situated preferably at a distance d from the tip of the tool, d being between 2 mm and 5 mm. Two examples for this type of tool are presented in FIGS. 4*a* and 4*b*.

Figure 4B:
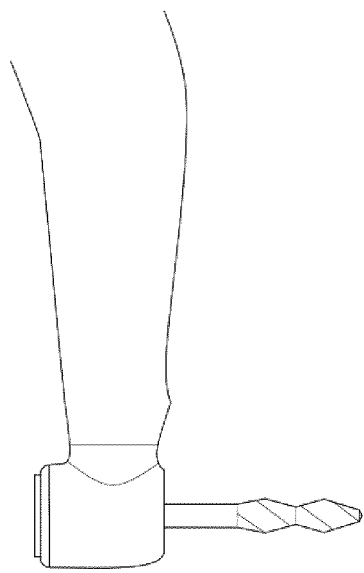
FIGS. 4A and 4B illustrate two different types of drill bits which can be used in the context of the present invention.
Figure 4A:
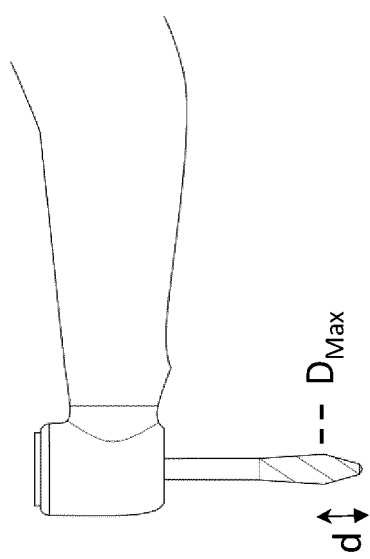

FIG. 4*a* illustrates a special drilling tool connected to a contra-angle, being characterized by a section of variable diameter with a "min-max-min" profile, the portion characterized by the maximum diameter having length $L_f$ (also referred to as $L_F$, e.g. on FIG. 5 discussed hereafter), while FIG. 4*b* is a special drilling tool connected to a contra-angle, characterized, for its part, by a section of variable diameter with a "min-max-min-max-min" profile. The special tool represented in FIG. 4*b* results in the additional advantage of ensuring the optimum tapping of the bone hole (i.e. the creation of the threaded hole, as for the standard drilling tools) and furnishing an accurate measuring of the cortical-trabecular separation (like the tool represented in FIG. 4*a*):

the 'first' portion (i.e. the one entering the first in the bone) characterized by the maximum diameter (over the length $L_F$) is the 'probe', having the role of measuring the current or the current derivative, thus evaluating the bone quality and identifying the cortical-trabecular separation.

The 'second' portion characterized by the maximum diameter (over a length $L_{F2}$) has the role of completing the tapping operation if the first portion is too short ($L_F \ll L_{F2}$) for creating directly the optimal screw thread of the hole.

The use of the special drilling tool of FIG. 4*b*, thus allows for avoiding an additional operation of tapping of the bone hole for creating the optimal screw thread for the subsequent implant. Obviously, if the entering of first portion of maximum diameter (i.e. the 'probe'), and the corresponding evaluation of the electric current derivative (and/or torque derivative) suggests a too poor bone quality, the drilling and tapping operation can be immediately stopped before that the 'second' part of maximum diameter enter in the cortical zone, thus minimizing the bone lesion.

The diameter of the drill bit is optimized to reduce the number of drilling phases (thus the risks associated with repeated actions, with vibrations and heat generated) without excessively increasing the risk of incorrect drilling (drilling directly at an excessive diameter risks causing an overheating and/or incipient cracks of the bone). Currently, the majority of manufacturers of drill bits recommend drilling in 3 phases:

1. Drilling with drill bit of 2.2 mm diameter
2. Drilling with drill bit of 2.8 mm diameter
3. Drilling with drill bit of 3.0 or 3.2 mm diameter The drilling quality is based on 3 qualitative criteria:

1. No fissure of the bone crossing the drill hole diametrically
2. Direction of the hole substantially perpendicular to the osseous surface
3. Low level of heat in the drilled area (parameter not precisely measurable)

The choice between different possible drill bit profiles thus provides an increased flexibility in terms of optimization of choices of operating protocols for the surgeon.

Furthermore, according to a preferred embodiment, following the results of measurement and the determination of the osseous quality in which the implant must be carried out, an optimization program installed on the console makes it possible to automatically pre-select specific suitable programs based on the results connected with the detected osseous quality following the drilling operation for the previously mentioned subsequent drilling phases. This makes it possible, for example, to adjust the size of the drill bit to be used for the following drilling phases or even the speed of the motor, or moreover determine an automatic limitation of the applicable torque so as not to damage the bone.

Thus, the device and the method disclosed within the framework of the present invention make it possible to obtain a more precise quantitative measurement of the osseous quality, and in particular to measure the local thickness of the cortical region of the bone.

This device and this measuring method are moreover suitable for a large number of commercially available drilling tools, and have the advantage of being able to be used in combination with a motor and a standard commercially available contra-angle (after calibration).

This device and this method can furthermore be used with special drilling tools (which can be provided with the implantology kit) which make it possible to obtain an even greater degree of measurement precision, in the case of patients deemed critical.

According the preferred embodiment r described hereinbefore, the quality of an osseous structure is determined through a first step (A) of drilling into the said osseous structure with the aid of a drilling tool such as a drill bit driven by a motor, and a second step (B) of simultaneous measurement of current consumption by the motor during the first step (A) of drilling, followed by a third step (C) of processing of the current consumption signal obtained following the second step (B) to obtain values of torque applied by the motor to the said drilling tool, and finally a fourth step (D) of correlation of the torque values obtained following the third step (C) with the speed of rotation of the said motor and the type of the said drill used during the first step (A) of drilling in order to deduce from this a relationship between the obtained torque values and the depth of the said osseous structure. According to this method, the relationship between the torque values and the depth of the osseous structure obtained following this fourth step (D) makes it possible moreover to determine the mechanical resistance to the drilling of the said osseous structure as a function of the depth.

Then, the relationship between the torque values and the depth of the osseous structure obtained following the fourth step (D) makes it possible moreover to identify zones of substantially constant mechanical resistance to the drilling and their associated levels of depth by calculating the derivative of the torque values as a function of depth. It may then further comprise a subsequent step of typological classification according to discrete values for the osseous structure studied, depending directly on the torque derivative (e.g. the drilling resistances $r_c$ & $r_t$ of the cortical and trabecular regions, respectively).

However, according to yet another preferred embodiment for the present invention, another current related value is used as an input parameter, namely current derivative. It that case, instead of measuring current values, current derivative values are sampled directly by the measurement unit.

Figure 5:
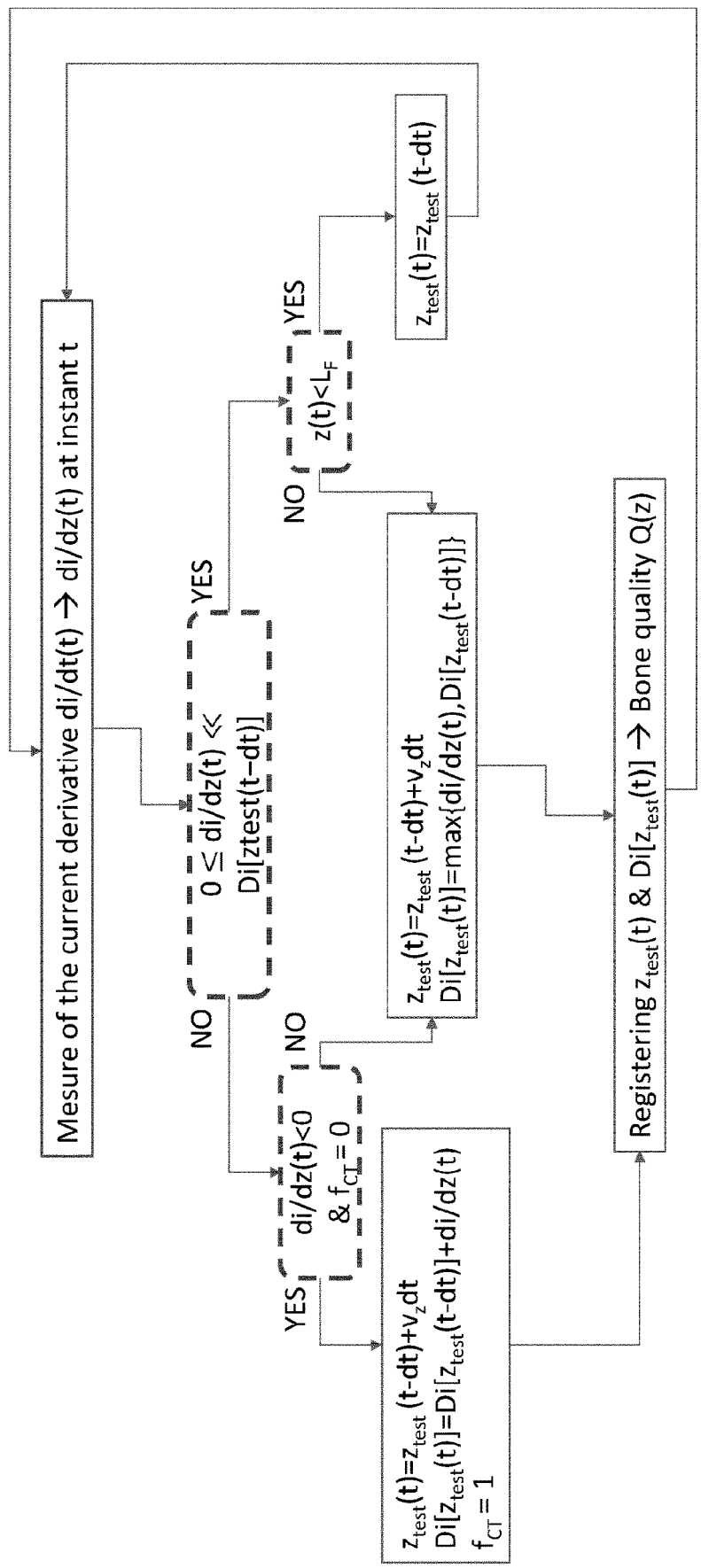
FIG. 5 illustrates a state diagram showing how bone quality values are yielded directly as a function of derivative of current values, according to a preferred embodiment for the present invention.

The state diagram of FIG. 5 explains how current derivative values are processed, depending on the current depth z(t) which depends on the rotational speed of the motor, in order to yield bone quality values, i.e. osseous quality values as a function of the depth z.

The procedure is summarized by the following steps (in this detailed description, we consider that the length $L_F$ of the active part of the drilling tool is longer than the depth corresponding to the separation between the cortical and the trabecular region):

1. The calculated quantity $z_{test}$, identifying the real penetration depth in the bone, is initialized to zero. Di[$z_{test}$(0)] is also initialized to zero. The discrete variable $f_{CT}$ indicating the crossing of the separation between the cortical and the trabecular regions is initialized to zero too ($f_{CT}$ will be zero until the drilling tool crosses the separation between the cortical and the trabecular regions).
2. Before the penetration in the bone, the value of the electric current derivative is almost zero, apart for the noise fluctuations mainly due to the yield of the contra-angle and the motor. Thus, the first logic bloc is obviously satisfied (YES). Since z(t) is smaller than the length of the active part of the drilling tool ($L_F$), $z_{test}$ is not incremented until the drilling tool enters into the bone.
3. The instant the drilling tool enters the cortical region of the bone (i.e. the external region of the bone), the derivative di/dz becomes positive. The first logic block is not satisfied (NO), as well as the second bloc (because the derivative di/dz is positive): thus the real depth $z_{test}$ is incremented (taking into account the actual speed of the tool) and the quantity Di, corresponding to the incremented value of $z_{test}$ takes the value di/dz.
4. While the drilling tool (or part of it) is inside the cortical region (i.e. before crossing the separation between the cortical and trabecular region), the derivative of the electric current is almost constant (except for small fluctuations due to signal noise or for a slow and slight increase due to the slight increase of the bone density inside the cortical region), because the linear increment of the penetration length (and of the contact surface between the drilling tool and the cortical material) corresponds to the linear increment of the required torque and electric current. The first and second logic blocs are not satisfied (both take the value "NO"). Thus the real depth $z_{test}$ is incremented and the quantity Di is either constant or takes the new value of di/dz, if this latter is slightly bigger than the previous one.
5. When the drilling tool reaches the separation between the cortical and the trabecular region, without being completely engaged inside the cortical region, the electric current derivative (and the torque derivative) decreases suddenly (to zero or to a positive value much smaller than the previous value): the further advancing of the drilling tool inside the bone (i.e. the trabecular region of the bone) does not require a relevant additional current supply. The first logic bloc is satisfied (YES) as well as the second logic bloc (in this case the drilling tool is longer than the depth corresponding to the separation between the cortical and trabecular regions). Thus, the real depth $z_{test}$ is not incremented.
6. The real depth is not incremented until the active part of the drilling tool is partially outside the bone (i.e. until the portion of the drilling tool inside the cortical region is constant). When the drilling tool is completely inside the bone and the portion of drilling tool inside the cortical region starts to decrease, the current derivative becomes negative: the contribution due to the additional trabecular material in contact with the drilling tool does not compensate the decrease of the amount of cortical material in contact with the active part of the drilling tool. Thus, the first logic bloc is not satisfied (NO), while the second logic bloc is satisfied (YES: the derivative is negative and $f_{CT}$ is still zero). The real depth $z_{test}$ is increased while the 'incremental current derivative' Di is reduced (because the current derivative di/dz is negative). The separation between the cortical and the trabecular region is reached, thus $f_{CT}$ is turned to 1.
7. The current derivative is negative until the active portion of the drilling tool is completely inside the trabecular region. Starting from this point, the current derivative is close to zero (apart for signal noise and slight inhomogeneities). Since $f_{CT}$ is 1, both the first logic bloc and the second logic bloc are not satisfied, thus the real depth is incremented until the end of the measurement.

In the case a special drilling tool (like the one in FIG. 4a), with an active portion shorter than the depth of separation between the cortical and trabecular regions is used, the procedure is modified starting from the point 5. In this case, the derivative of the electric current decreases suddenly to zero or to a very low value when the active portion of the drilling tool is completely inside the cortical region (i.e before reaching the separation between the cortical and trabecular regions). In this case, the second logic bloc on the right part of the state diagram is not satisfied when the derivative is zero or close to zero. Thus the incremental current derivative Di remains constant until the active portion of the drilling tool is inside the cortical region. Also for a special tool like the one in FIG. 4a, the points 6 and 7 remains valid: the negative value of the derivative di/dz results in the reduction of the incremental current derivative Di, accounting for the decreased density and/or hardness of the trabecular region.

The outlined procedure allows for clearly identify two values accounting for the cortical and trabecular bone quality, respectively. In addition it allows for identifying the depth of the separation between the cortical and trabecular regions.

Using current derivative values instead of current values as an input parameter in order to yield torque derivative values, and thus osseous quality values, has following advantages. First, it saves significant computing steps as compared to a method where it is first necessary to post-process current values in order to correlate these values to torque values first, and then derive the torque derivative curve from these latter values. Secondly, torque values are affected by the performance of the handpiece and of the motor itself, which may vary over time, depending on they age and on the lubrication conditions; therefore, the measurements provided do not depend exclusively on the bone density and hardness, and therefore its associated quality. Thirdly, torque measurement depends intrinsically on the mechanical resistance applied by the bone on the drilling tool, integrated spatially over the whole length of the drilling tool inserted into the bone at a given instant. It is thus not a local measurement allowing to determine the density and hardness locally, at a very specific spot.

This computation method hence allows to more easily identify regions of homogeneous density and hardness such as the trabecular region and cortical regions, showing drilling resistances $r_c$ & $r_t$ respectively.

Figures 6A, 6B:
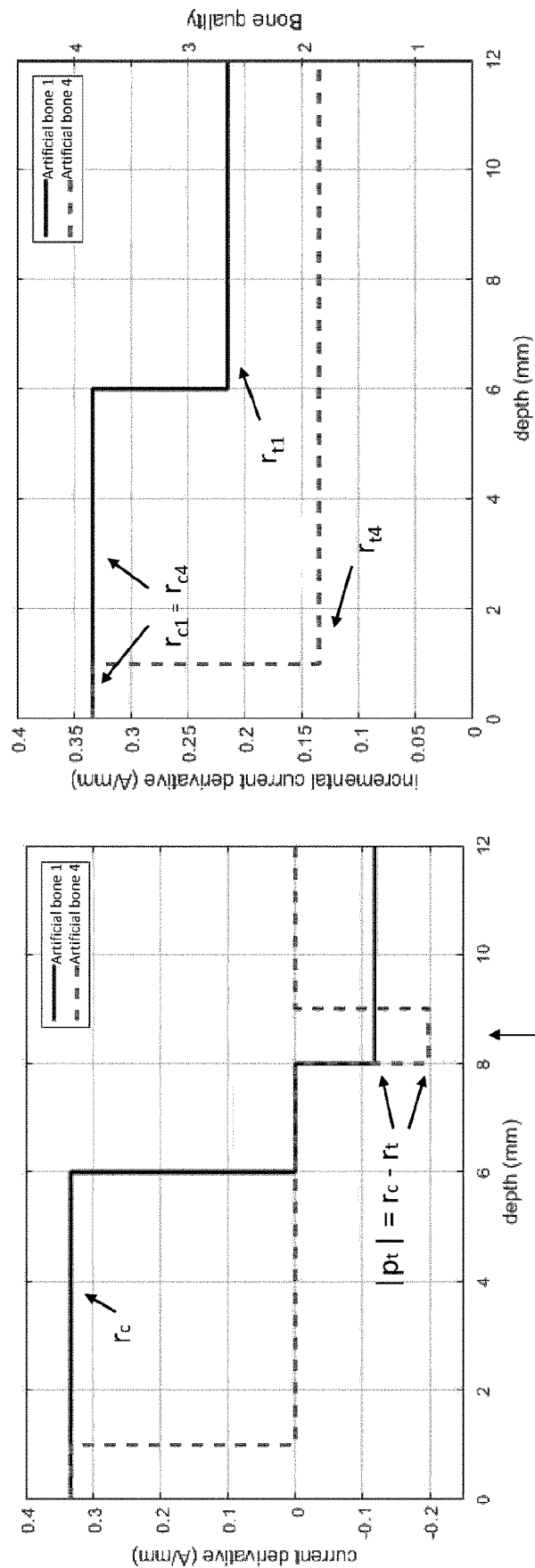
FIGS. 6A and 6B show respectively a graph of current derivative of the current consumed by the motor for the two different types of artificial bone illustrated previously on FIGS. 3A and 3B as a function of depth, and a schema of the resulting bone quality also as a function of the depth in each of the two bones.

These drilling resistances $r_c$ & $r_t$ previously illustrated on FIG. 3B can be obtained in an even more intuitive way further in view of FIGS. 6A & 6B, showing graphs of current derivate as a function of the depth for the same artificial bones when drilled by the same drill bit having a length of 8 mm. Indeed, the constant derivative of the torque as a function of depth (z) indicates a homogeneous drilling resistance re over the cortical region, instead of being derived of an initial slope. Then, when the derivative becomes negative after the depth exceeds the length of the drill bit (i.e. 8 mm), the value $|pt|=r_c-r_t$ can be obtained and in turn the resistance in the trabecular region $r_t$. Thus, the measurement can be stopped as of this depth because all resistance values are determined, and therefore the $P_{end\_of\_measurement}$ can be set at about 9 mm, as indicated on FIG. 6A.

FIG. 6B shows how incremental current derivative values can be mapped directly to drilling resistance values for each of the bone types, i.e. artificial bone 1 & artificial bone 4, therefore allowing for a very straightforward mapping with an osseous quality scale (on the right of FIG. 6B). In the present case, we have $r_{c1}=r_{c4}$ which is approximately equal to 0.34 A/mm, while $r_{t1}=0.22$ A/mm et $r_{t4}=0.14$ A/mm. These values correspond to the values previously obtained via the spatial derivation of the torque, the mathematical relation between the corresponding values being:

$$x \eta k_t Di = dC/dz$$

where x is the multiplication factor (20 if the contra-angle is a 20:1 CA), η is the yield of the CA and $k_t$ is the torque constant of the motor (defining the value the torque proportional to the supplied current).

Figure 7B:
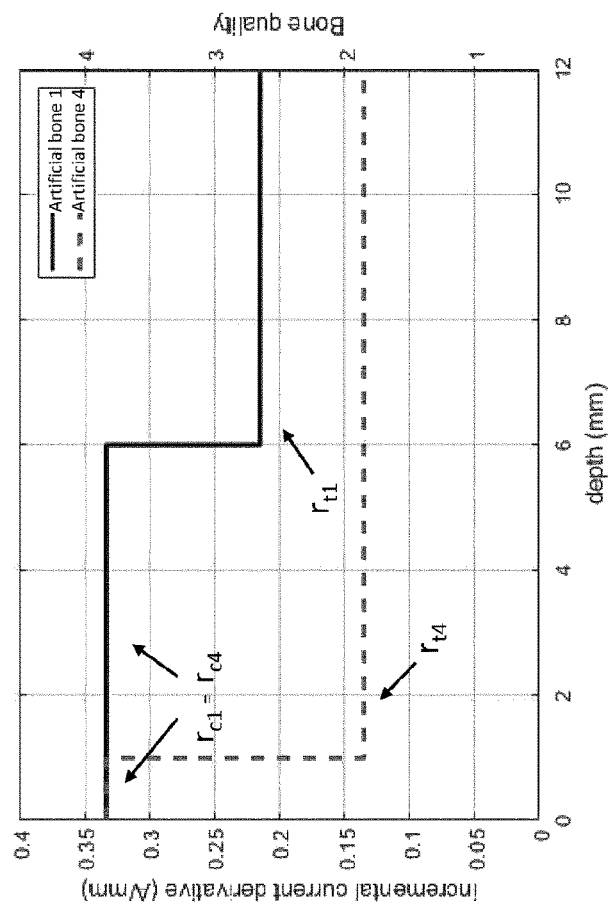
Figure 7A:
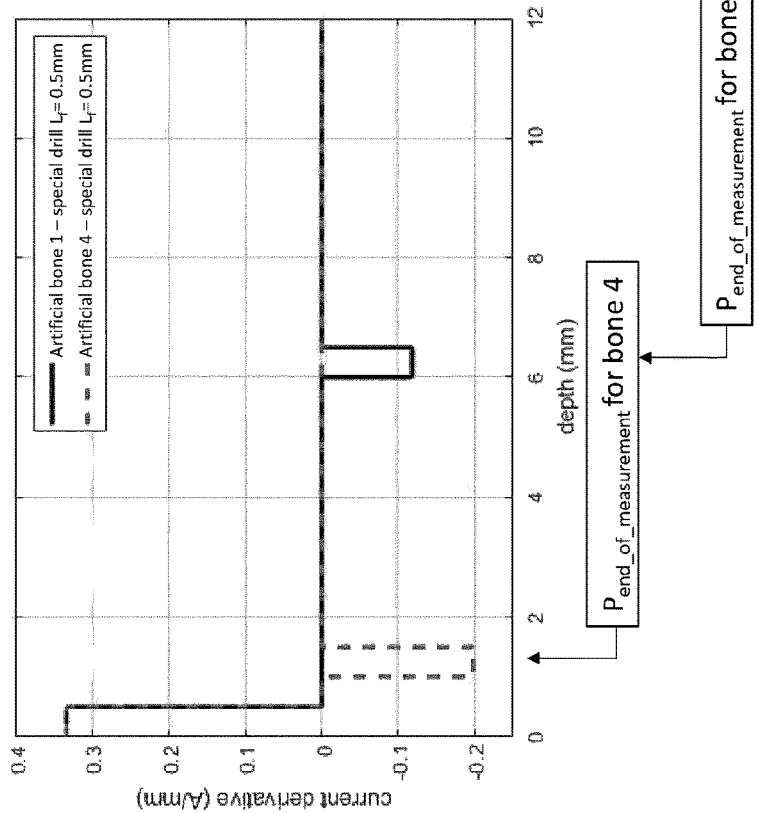

FIGS. 7A & 7B show of the drilling resistance values can be further obtained with a special drill such as the one disclosed on FIG. 4A, having a reduced length $L_f$ corresponding to the portion where the diameter is maximal. These figures yield the same values for the drilling resistances (in fact, FIGS. 6B & 7B are identical); however, the reduced length of the drill, which becomes inferior to the depth of the cortical region, allows to have the following advantageous properties: the derivate falls down to zero as soon as the drill bit is completely engaged into the this zone (see the drop at z=0.5 on FIG. 7A) and depth at which the measurements can be stopped $P_{end\_of\_measurement}$ can then right be after the end of the respective cortical regions, i.e. about 1.5 mm for artificial bone 4, and 6.5 mm for artificial bone 1. As a result, the overall drilling operation can be shorter, and this operation can also be less invasive and generate less heating due to friction.

Another advantage of employing this computation method with current derivative values as input and this special drill is that the respective resistance values for the cortical regions and the trabecular regions are yielded by derivative values of opposite signs. The crossover with change of signs of the derivative allows to reduce the impact of noise on the measures.

However, irrespective of the type of drill used, it can be appreciated that using current derivative values as inputs allow to easily identify the transition between regions, where the derivative values significantly jump from on discrete value to another. The results provided are hence more accurate and reliable while simultaneously dispensing of any post-processing of the input signal.

In the framework of the present invention, it is also possible to provide more accurate results in terms of 3D modelling of the quality of an osseous structure. Indeed, as illustrated on FIGS. 8A & 8B, it may well be that the transition between regions is not a clear-cut according to a horizontal plane, but instead that there is some partial vertical overlap. The sagittal sectional view of FIG. 8A highlights the vertical interlocking of the trabecular region with the cortical region, while the sectional view in the horizontal plane A-A shows how the angular proportion of the overstacked trabecular region.

In order to be able to quantify more precisely the osseous quality, the device according to the present invention is preferably arranged for sampling current related values at a rate of at least 10 times for each complete revolution of the drill bit. If the reduction ratio of the handpiece is chosen to be equal 20:1, and that the motor speed is about 400 rpms, then the device gathers at least 5 measurement data per second; the drill bit effects a complete revolution every three seconds and therefore 15 measurement data are available for each revolution of the drill bit. It is thus possible to obtain a good angular distribution of the osseous quality; the dispersion of data over a complete revolution of the drill bit gives an idea of the amplitude of local variations affecting the density/hardness according to different orientations.

Figure 9B:
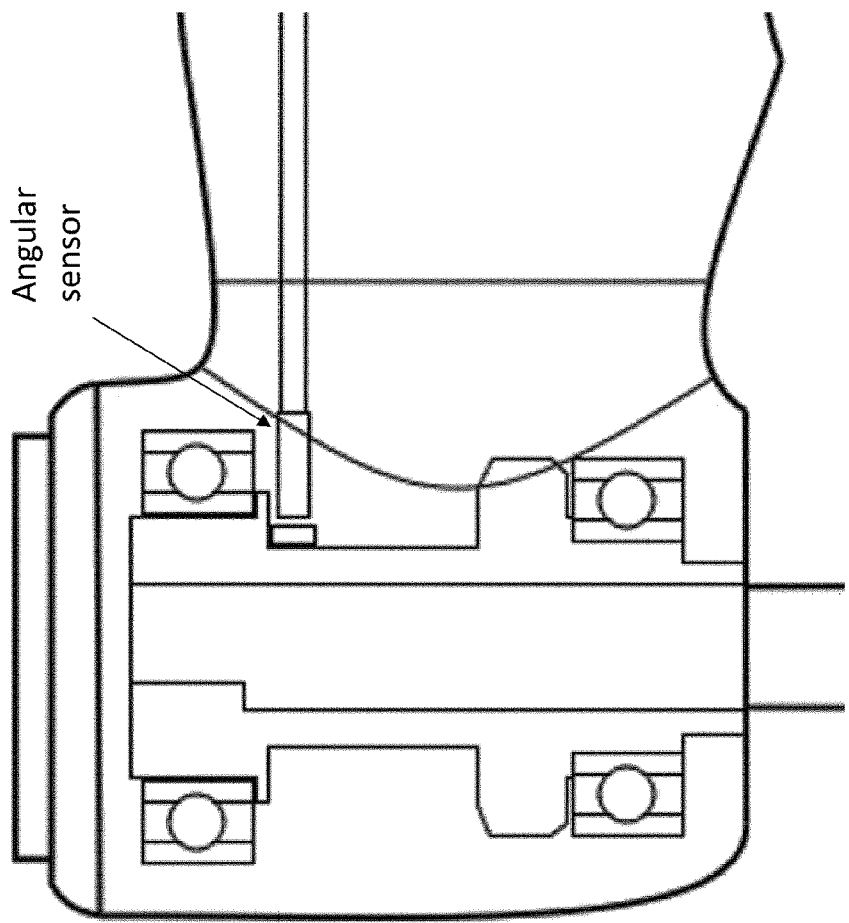
FIGS. 9A and 9B show respectively a sagittal section view of handpiece on which the drill bit is mounted comprising an angular sensor according to a preferred embodiment for the present invention, and an enlarged view of this angular sensor mounted on the handpiece.
Figure 9A:
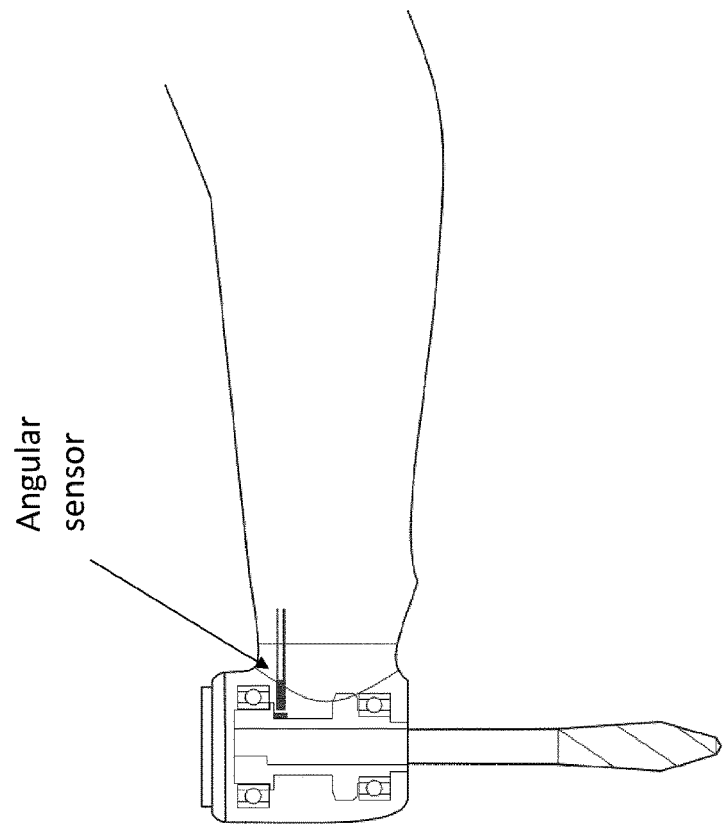

The device for determining the quality of an osseous structure also preferably encompasses a indexing system based on an angular sensor in order to know the exact orientation of the rotor of the contra-angle and thus of the drill bit. As illustrated on FIGS. 9a & 9b, the angular sensor can for example be a Hall sensor, magnetic sensor, optical sensor of electrical sensor. This way, by ensuring that the relative angular orientation of the drill bit with respect to the angular position of the motor is always known, it is possible to determine the exact orientation of the drill bit inside the bone.

Figure 10:
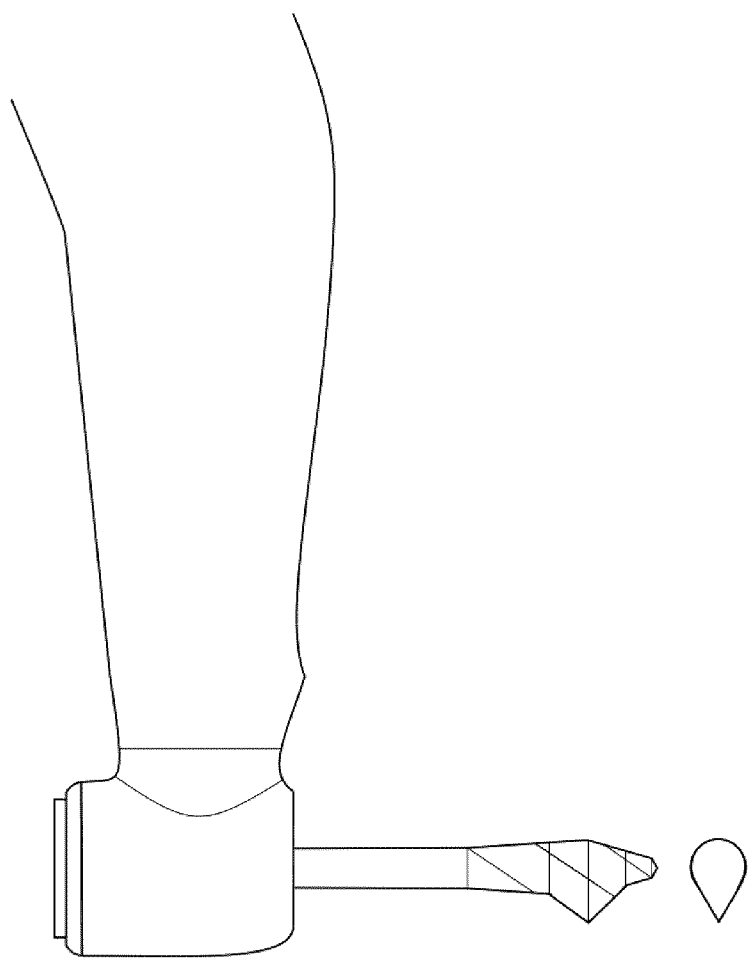
FIG. 10 shows a side view of a handpiece according to a preferred embodiment for the present invention comprising an asymmetrical drilling bit.

Thus, when further providing the device for determining the quality of an osseous structure comprises a non-circular asymmetrical drill bit, yielding an extruded diameter is at least 20% greater than the mean diameter of the drill bit, it is possible to obtain a 3D representation of the bone quality, because it is possible to know not only the variation of the bone quality as a function of the penetration depth, but also as a function of the angular orientation. An example of such asymmetrical drill bit is illustrated on FIG. 10.

Figure 11:
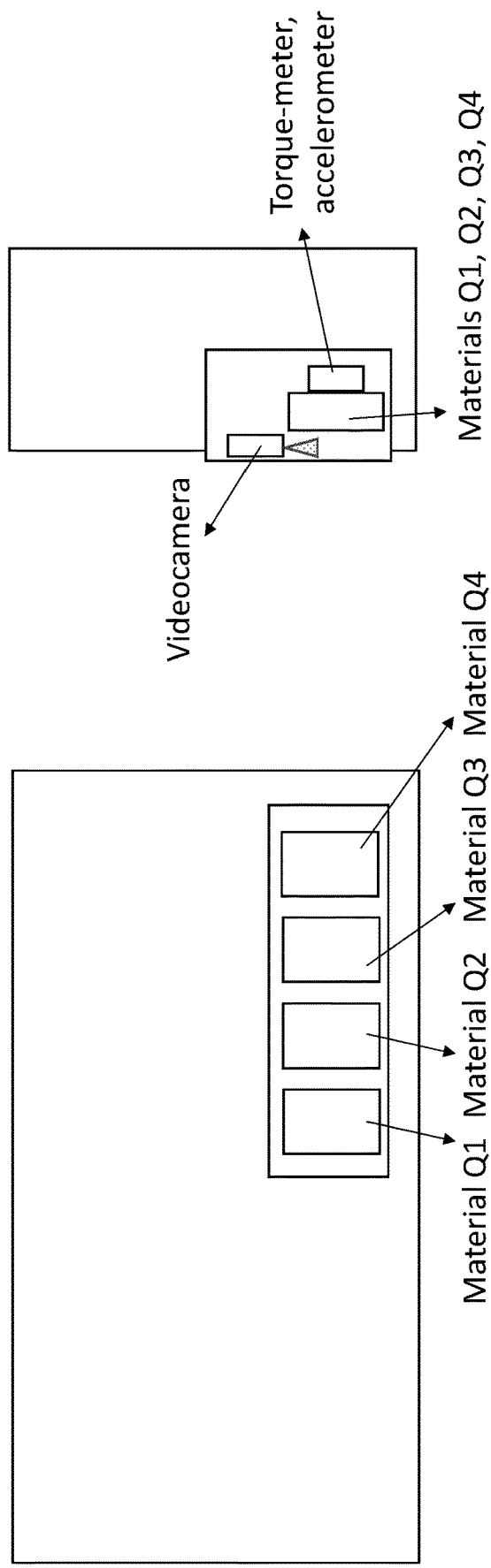
FIG. 11 shows a schematical view of a calibration tool according to another preferred embodiment for the present invention.

According to a variant embodiment for the present invention, the device for determining the quality of an osseous structure further encompasses a calibration and benchmarking tool, allowing to define classification criteria according to a specific drilling bit, contra-angle handpiece or motor. An example for such a calibration system is illustrated on FIG. 11, where the left part of the figure shows the different benchmark pieces of material to be drilled, and on the right part, a schematic view of a contra-angle handpiece fitted with torquemeter, accelerometer and also video camera, in a modular fashion or not.

By way of example, the following calibration procedure could be carried out:
  Gathering an image of the drilling bit via the camera integrated to the dental unit, tabletop control unit, or to the modular calibration system. The tail of the drill bit being normalized, it is then easy to obtain the scale of the image and in turn extract the active diameter and the active length of the drilling tool;
  Measure the current derivative data when drilling with the mounted drill bit into samples of material (here 4 samples, i.e. Q1,Q2,Q3,Q4); the measurement of the initial derivative values are enough to set parameters of osseous quality;
  As an alternative to the previous calibration step, measure the torque applied at the tip of the drill bit (via a torquemeter, such as a sleeve out of resin applying an adjustable friction on the top of case, if the correlation scale between torque values and reference osseous quality have been established, there is no need to have several blocks of material, one is then enough;
  Controlling the rotation speed via an accelerometer & video camera when drilling in order to check the consistency of the speed: if the speed is shaky, after sale intervention is required or the drill bit is to be considered as not suitable.

This way, there is no need for an update of databases and/or invention of after sale forces when a new drill bit, a new handpiece, or a new motor compliant with the device are launched on the market.

It will be appreciated from the preceding description that the features of the preferred embodiments detailed hereinbefore can be combined as desired, and especially features relating to the drill bit can be used irrespective of the input parameter used for computing the torques derivative values, and hence the osseous quality.

The invention claimed is:

1. Device for determining the quality of an osseous structure, comprising a device for controlling a motor connected kinematically to a drilling tool including a drill bit, a measuring unit for instantly calculating current derivative values for current consumed by said motor during a drilling operation, as well as a processing unit configured to process data collected by the measuring unit simultaneously with the said drilling operation, said processing unit being further configured to process the current derivative values in order to directly yield values for a derivative of torque applied by said motor to said drilling tool, and to correlate said values for the derivative of torque with a speed of rotation of said motor and a type of drill used during said drilling operation in order to deduce a relationship between said values for the derivative of torque and a depth of said osseous structure, wherein said values for the derivative of torque correspond to a drilling resistance that defines the quality of the osseuous structure.

2. Device for determining the quality of an osseous structure according to claim 1, further comprising an indexing system for the drill bit and an angular sensor in order to know an exact orientation of the drill bit.

3. Device for determining the quality of an osseous structure according to claim 2, wherein said measuring unit is arranged for sampling said current derivative values at a rate of at least 10 times for each complete revolution of the drill bit.

4. Device for determining the quality of an osseous structure according to claim 3, said drill bit being of asymmetrical section yielding an extruded diameter of at least 20% greater than a mean diameter of the drill bit.

5. Device for determining the quality of an osseous structure according to claim 1, further comprising a console equipped with a display unit and a control interface allowing a surgeon to determine the type of drill used and to set the speed of rotation of the motor.

6. Device for determining the quality of an osseous structure according claim 5, wherein said console automatically pre-selects suitable specific programs based on the quality of the osseuous structure following the drilling operation.

7. Device for determining the quality of an osseous structure according to claim 1, wherein values for the derivative of torque that are constant over a given depth allows to identify regions of homogeneous density and hardness, classified into distinct classes of osseous quality.

8. Device for determining the quality of an osseous structure according to claim 1, wherein said drill bit has a variable diameter profile ranging between a minimal value and a maximal value, a ratio between the minimal value and the maximal value being at least equal to 2.

9. Device for determining the quality of an osseous structure according to claim 1, further comprising a calibration and benchmarking tool adapted for specific contra-angle handpieces, drill bits, and/or motors.

10. Device for determining the quality of an osseous structure according to claim 1, wherein the drill bit is mounted in removable fashion on a contra-angle handpiece determining a predetermined gear ratio and being compatible with a plurality of types of different drills.

11. Device for determining the quality of an osseous structure according to claim 1, wherein said device is arranged for yielding two distinct values accounting for cortical and trabecular bone quality, respectively, and to identify a depth of the separation between the cortical and trabecular regions of a bone.

12. Device for determining the quality of an osseous structure according to claim 1, further comprising a wireless communication interface for transmission of measurement data.

* * * * *